(12) United States Patent
Niver et al.

(10) Patent No.: US 12,220,123 B2
(45) Date of Patent: Feb. 11, 2025

(54) APPARATUS AND METHODS FOR JOINING BONES

(71) Applicant: Medline Industries, LP, Northfield, IL (US)

(72) Inventors: Ryan Niver, Glenview, IL (US); Michael Ksenich, Northfield, IL (US); Dinesh Koka, Winter Park, FL (US)

(73) Assignee: Medline Industries, LP, Northfield, IL (US)

( * ) Notice: Subject to any disclaimer, the term of this patent is extended or adjusted under 35 U.S.C. 154(b) by 577 days.

(21) Appl. No.: 17/407,182

(22) Filed: Aug. 19, 2021

(65) Prior Publication Data

US 2023/0060073 A1 Feb. 23, 2023

(51) Int. Cl.
*A61B 17/064* (2006.01)
*A61B 17/16* (2006.01)
*A61B 17/17* (2006.01)

(52) U.S. Cl.
CPC ...... *A61B 17/0642* (2013.01); *A61B 17/1615* (2013.01); *A61B 17/1728* (2013.01);
(Continued)

(58) Field of Classification Search
CPC ............ A61B 17/0642; A61B 17/1615; A61B 17/1728; A61B 17/17; A61B 17/1775; A61B 17/0641; A61B 17/0648; A61B 17/064; A61B 17/068; A61B 17/0682; A61B 17/1714; A61B 17/1682; A61B 17/1739; A61B 17/1782; A61B 2017/0641; A61B 2017/0648
(Continued)

(56) References Cited

U.S. PATENT DOCUMENTS

| 294,777 | A | 3/1884 | Forbes |
| 324,126 | A | 8/1885 | Le Gay |

(Continued)

FOREIGN PATENT DOCUMENTS

| EP | 0127994 | 12/1984 |
| FR | 2628312 | 9/1989 |

(Continued)

OTHER PUBLICATIONS

Stryker, EasyClip Osteosynthesis Compression Staples brochure, bearing a copyright date of 2015.
(Continued)

*Primary Examiner* — Marcela I. Shirsat
(74) *Attorney, Agent, or Firm* — Fitch, Even, Tabin & Flannery LLP

(57) ABSTRACT

Apparatus and methods are described for use in securing a first bone relative to a second bone using a pair of surgical staples or, alternatively, a surgical staple and a bone screw. When a pair of staples are used, one of the legs of one of the staples may pass between the legs of the another of the staples. When a staple and a bone screw are used, the bone screw may pass between the legs of the staple. A guide tool can be used during the drilling of the holes for the legs of the staples or the legs of the staple and a bone screw. The guide tool provides guides for drilling guide holes for the staples or for the screw and staple. The guides can be fixed relative to each other during drilling of the guide holes.

25 Claims, 12 Drawing Sheets

(52) U.S. Cl.
CPC ............... *A61B 2017/0641* (2013.01); *A61B 2017/0648* (2013.01); *A61B 17/1682* (2013.01); *A61B 17/1714* (2013.01); *A61B 17/1739* (2013.01); *A61B 17/1775* (2016.11); *A61B 17/1782* (2016.11)

(58) Field of Classification Search
USPC .......................................................... 606/75
See application file for complete search history.

(56) References Cited

U.S. PATENT DOCUMENTS

| | | | |
|---|---|---|---|
| D28,350 S | 3/1898 | Reuter | |
| D29,472 S | 10/1898 | Hughes et al. | |
| 1,257,807 A | 2/1918 | Carrell | |
| 1,354,737 A | 10/1920 | Frisk | |
| 1,639,530 A | 8/1927 | Payson | |
| 2,067,359 A | 1/1937 | Tumminello | |
| 2,174,708 A | 10/1939 | Sears | |
| 3,154,999 A | 11/1964 | Stewart | |
| 3,316,794 A | 5/1967 | Dixon | |
| 3,564,663 A | 2/1971 | Roberts | |
| 3,584,347 A | 6/1971 | Klenz | |
| 3,787,608 A | 1/1974 | Colby | |
| 3,821,919 A | 7/1974 | Knohl | |
| 3,824,995 A | 7/1974 | Getscher | |
| 3,940,844 A | 3/1976 | Colby | |
| 3,960,147 A | 6/1976 | Murray | |
| D243,365 S | 2/1977 | Cross | |
| 4,263,903 A | 4/1981 | Griggs | |
| 4,454,875 A | 6/1984 | Pratt | |
| D281,814 S | 12/1985 | Pratt | |
| 4,565,193 A | 1/1986 | Streli | |
| 4,570,623 A | 2/1986 | Ellison | |
| 4,592,346 A | 6/1986 | Jurgutis | |
| D286,442 S | 10/1986 | Korthoff | |
| 4,799,481 A | 1/1989 | Transue | |
| 4,848,328 A | 7/1989 | Laboureau | |
| 5,179,964 A | 1/1993 | Cook | |
| 5,263,973 A | 11/1993 | Cook | |
| 5,449,359 A | 9/1995 | Groiso | |
| 5,454,814 A | 10/1995 | Comte | |
| 5,662,655 A | 9/1997 | Laboureau | |
| 5,674,222 A | 10/1997 | Berger | |
| 5,785,713 A | 7/1998 | Jobe | |
| 5,853,414 A | 12/1998 | Groiso | |
| 5,941,890 A | 8/1999 | Voegele | |
| 6,001,110 A | 12/1999 | Adams | |
| 6,120,511 A * | 9/2000 | Chan ................ | A61B 17/1637 606/179 |
| 6,187,009 B1 | 2/2001 | Herzog | |
| 6,325,805 B1 | 12/2001 | Ogilvie | |
| 6,336,928 B1 | 1/2002 | Guerin | |
| 6,401,306 B1 | 6/2002 | Hanten | |
| 6,652,592 B1 | 11/2003 | Grooms | |
| 6,767,356 B2 | 7/2004 | Kanner | |
| 6,773,437 B2 | 8/2004 | Ogilvie | |
| 7,108,697 B2 | 9/2006 | Mingozzi | |
| D572,363 S | 7/2008 | Menn | |
| D587,370 S | 2/2009 | Coillard-Lavirotte | |
| D596,294 S | 7/2009 | Coillard-Lavirotte | |
| 7,722,610 B2 | 5/2010 | Viola | |
| 7,794,475 B2 | 9/2010 | Hess | |
| 7,824,426 B2 | 11/2010 | Racenet | |
| 8,021,389 B2 | 9/2011 | Molz, IV | |
| 8,360,297 B2 | 1/2013 | Shelton, IV | |
| 8,366,748 B2 | 2/2013 | Kleiner | |
| 8,393,517 B2 | 3/2013 | Milo | |
| 8,584,853 B2 | 11/2013 | Knight | |
| 8,596,514 B2 | 12/2013 | Miller | |
| 8,679,154 B2 | 3/2014 | Smith | |
| D705,930 S | 5/2014 | Cheney | |
| 8,720,766 B2 | 5/2014 | Hess | |
| D707,357 S | 6/2014 | Cheney | |
| 8,808,325 B2 | 8/2014 | Hess | |
| D728,103 S | 4/2015 | Katchis | |
| 9,039,737 B2 | 5/2015 | Vold | |
| 9,198,769 B2 | 12/2015 | Perrow | |
| 9,254,180 B2 | 2/2016 | Huitema | |
| 9,295,463 B2 | 3/2016 | Viola | |
| 9,339,268 B2 | 5/2016 | Fox | |
| 9,402,624 B1 | 8/2016 | Scott | |
| 9,433,452 B2 | 9/2016 | Weiner | |
| 9,463,260 B2 | 10/2016 | Stopek | |
| 9,486,212 B2 | 11/2016 | Miller | |
| D780,311 S | 2/2017 | Cheney | |
| 9,743,926 B2 | 8/2017 | Fox | |
| 9,855,036 B2 | 1/2018 | Palmer | |
| 9,901,338 B2 | 2/2018 | Anderson | |
| D826,405 S | 8/2018 | Shelton, IV | |
| 10,058,366 B2 | 8/2018 | Bouduban | |
| 10,064,619 B2 | 9/2018 | Palmer | |
| 10,064,623 B2 | 9/2018 | Soutorine | |
| 10,085,743 B2 | 10/2018 | Roedl | |
| 10,105,134 B2 | 10/2018 | Biedermann | |
| 10,117,647 B2 | 11/2018 | Cheney | |
| 10,130,358 B2 | 11/2018 | Palmer | |
| 10,166,022 B2 | 1/2019 | Early | |
| D840,035 S | 2/2019 | Weiner | |
| 10,238,382 B2 | 3/2019 | Terrill | |
| 10,307,156 B1 | 6/2019 | Blair | |
| D857,199 S | 8/2019 | Cheney | |
| 10,610,218 B2 | 4/2020 | Palmer et al. | |
| D886,299 S | 6/2020 | Cundiff | |
| D895,113 S | 9/2020 | Blair | |
| 10,779,816 B2 | 9/2020 | Goldstein | |
| 10,820,902 B2 | 11/2020 | Cheney | |
| 10,874,389 B2 | 12/2020 | Biedermann | |
| 10,918,484 B2 | 2/2021 | Ellington et al. | |
| 10,945,725 B2 | 3/2021 | Hollis | |
| 10,987,101 B2 | 4/2021 | Ducharme | |
| 11,000,323 B2 | 5/2021 | Stamp | |
| 11,006,949 B2 | 5/2021 | Daniel | |
| 11,020,110 B1 | 6/2021 | Blair | |
| 11,090,043 B2 | 8/2021 | Biedermann | |
| 11,116,499 B1 | 9/2021 | Blair | |
| 11,278,278 B2 | 3/2022 | Biedermann | |
| 11,284,886 B2 | 3/2022 | Hartdegen | |
| D957,636 S | 7/2022 | Blair | |
| 11,553,952 B2 | 1/2023 | Hammann | |
| 11,596,398 B2 | 3/2023 | Wahl | |
| 11,642,124 B2 | 5/2023 | Maclure et al. | |
| 11,653,913 B2 | 5/2023 | Goldstein et al. | |
| 11,684,359 B2 | 6/2023 | Biedermann | |
| 11,911,036 B2 | 2/2024 | Reed | |
| D1,017,038 S | 3/2024 | Bushko | |
| 11,937,819 B2 | 3/2024 | Pheil | |
| 2003/0225423 A1 | 12/2003 | Huitema | |
| 2004/0193188 A1 | 9/2004 | Francese | |
| 2005/0021035 A1 | 1/2005 | Groiso | |
| 2005/0288707 A1 | 12/2005 | De Canniere | |
| 2006/0058802 A1 | 3/2006 | Kofoed | |
| 2007/0233113 A1 | 10/2007 | Kaelblein | |
| 2007/0270906 A1 | 11/2007 | Molz | |
| 2007/0276388 A1 | 11/2007 | Robertson | |
| 2008/0147068 A1 | 6/2008 | Hashimoto | |
| 2009/0005809 A1 | 1/2009 | Hess | |
| 2011/0022099 A1 | 1/2011 | Ashman | |
| 2013/0231667 A1 | 9/2013 | Taylor | |
| 2013/0345752 A1 | 12/2013 | Hendren | |
| 2014/0276830 A1 | 9/2014 | Cheney | |
| 2014/0277516 A1 | 9/2014 | Miller | |
| 2014/0358187 A1 | 12/2014 | Taber | |
| 2015/0133940 A1 | 5/2015 | Palmer | |
| 2015/0313592 A1 | 11/2015 | Coillard-Lavirotte | |
| 2017/0000482 A1 | 1/2017 | Averous | |
| 2017/0252036 A1 | 9/2017 | Palmer et al. | |
| 2018/0271521 A1 | 9/2018 | Wahl | |
| 2018/0344316 A1 | 12/2018 | Palmer | |
| 2019/0046182 A1 | 2/2019 | Krumme | |
| 2019/0069892 A1 | 3/2019 | Biedermann | |
| 2019/0105040 A1 | 4/2019 | Gordon | |
| 2019/0115040 A1 | 4/2019 | Kamdar et al. | |
| 2020/0000046 A1 | 1/2020 | Orschulik | |

(56) References Cited

U.S. PATENT DOCUMENTS

| | | |
|---|---|---|
| 2020/0038076 A1 | 2/2020 | Amis |
| 2020/0046345 A1* | 2/2020 | Zink |
| 2021/0298748 A1* | 9/2021 | Campbell ............ A61B 17/864 |
| 2021/0330324 A1 | 10/2021 | Biedermann |
| 2021/0386422 A1 | 12/2021 | Maclure |
| 2022/0211368 A1 | 7/2022 | Hartdegen |
| 2023/0000488 A1 | 1/2023 | Palmer |
| 2023/0172647 A1 | 6/2023 | Knight |
| 2023/0200809 A1 | 6/2023 | Wahl |

FOREIGN PATENT DOCUMENTS

| | | |
|---|---|---|
| FR | 2694696 | 2/1994 |
| FR | 3023468 | 1/2016 |
| GB | 793126 | 4/1958 |
| IL | 64726 | 2/1985 |
| WO | 9616603 | 6/1996 |
| WO | 2006077878 | 7/2006 |
| WO | 201288575 | 7/2012 |

OTHER PUBLICATIONS

U. Rethnam et al., "Mechanical Characteristics of Three Staples Commonly Used in Foot Surgery," Journal of Foot and Ankle Research (Feb. 25, 2009).

Memometal Inc. USA, Easy Clip SI brochure, Aug. 12, 2009.

* cited by examiner

APPARATUS AND METHODS FOR JOINING BONES

FIELD

Apparatus and methods for joining or fusing two bones together are described herein and, more specifically, apparatus and methods for drilling guide holes in bones for receiving surgical staples or a surgical staple and a bone screw.

BACKGROUND

Screws are commonly used for joining or fusing two bones or bone pieces together. The screw or screws may cross a joint, fracture or osteotomy. For example, screws can be used to fuse metatarsal phalangeal (MTP) joints to relieve pain. By way of another example, screws can be used in a Lapidus procedure to fuse the joint between the first metatarsal bone and the medial cuneiform. Instead of screws, fusions can be made using compression staples. A problem with using screws or staples, particularly where multiple such fasteners are used in a single procedure, is that often guide holes for receiving the screws or legs of the staples are drilled free-hand. Although suitable fusions can be made using holes that are drilled free-hand, this can be time consuming and potentially prone to errors in the relative positions and orientations of the staple legs or screw.

The guide tools and methods described herein can address these problems.

DETAILED DESCRIPTION

As described herein and shown in FIGS. 1-25, apparatus and methods are disclosed for use in securing a first bone relative to a second bone using a pair of surgical staples or, alternatively, a surgical staple and a bone screw. When a pair of staples are used, advantageously at least one of the legs of one of the staples passes between the legs of the another of the staples. If the legs of the staple are coplanar, then this can beneficially result in intersecting planes of securement. When a staple and a bone screw are used, advantageously the bone screw passes between the legs of the staple. This can beneficially result in the bone screw intersecting a plane of the legs of the staple. A guide tool can be used during the drilling of the holes for the legs of the staples or the legs of the staple and a bone screw. Advantageously, the guide tool provides guides for drilling the guide holes such that the guides can be fixed relative to each other to improve accuracy during drilling and make the fusion procedure faster, simpler and readily reproducible.

Figure 10:
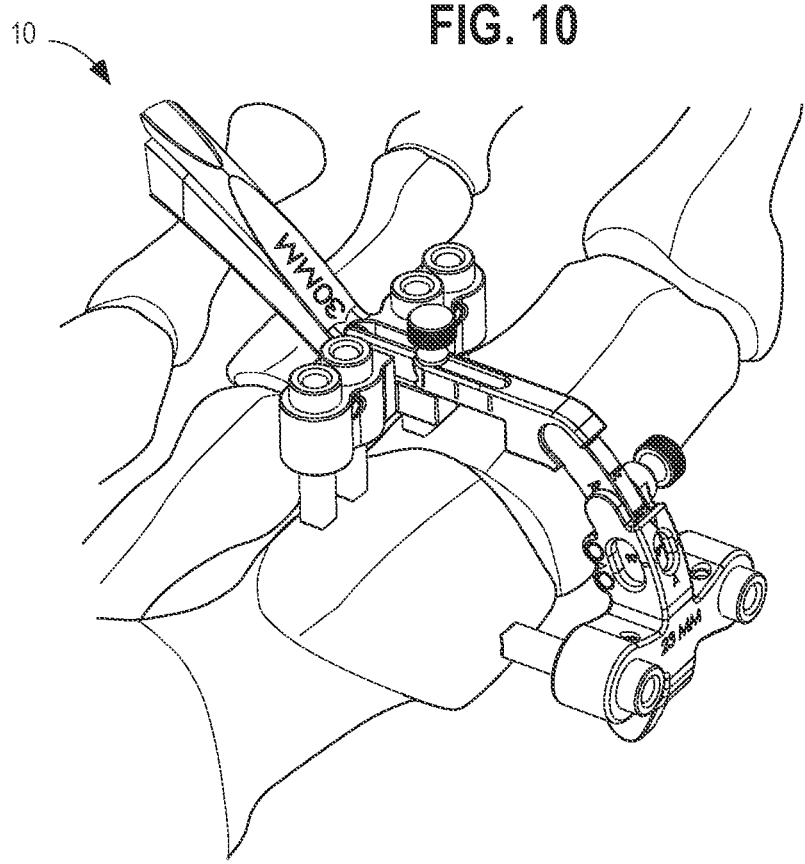
FIG. 10 is another perspective view of an operative portion of the guide tool of FIG. 1 positioned adjacent a bone in before guide holes have been drilled in the bone and before staples inserted into the guide holes.
Figure 11:
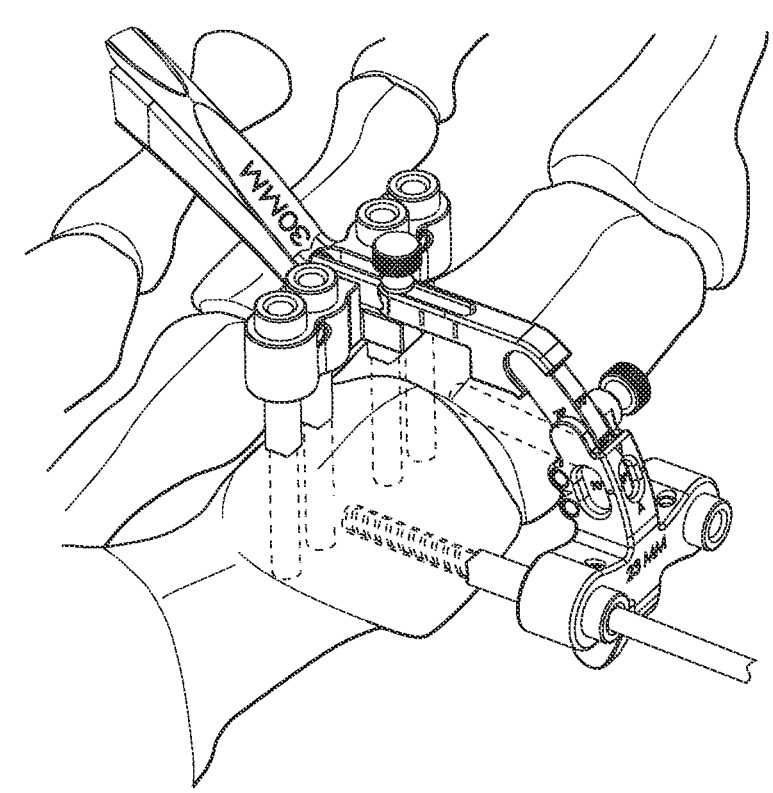
FIG. 11 is perspective view, similar to that of FIG. 10, of an operative portion of the guide tool of FIG. 1 positioned adjacent a bone in after some but not all of the guide holes have been drilled in the bone and before staples are inserted into the guide holes.
Figure 12:
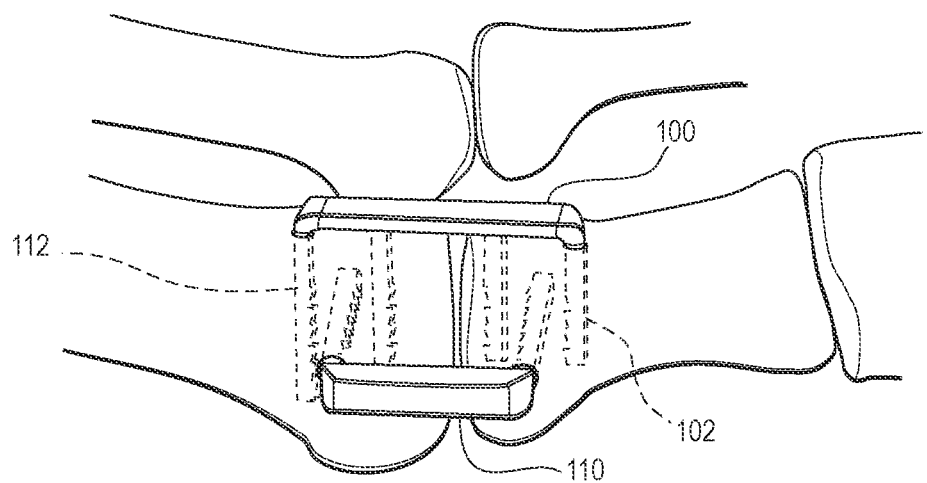
FIG. 12 is a perspective view of a pair of staples having been inserted into holes drilled in the bones.
Figure 20:
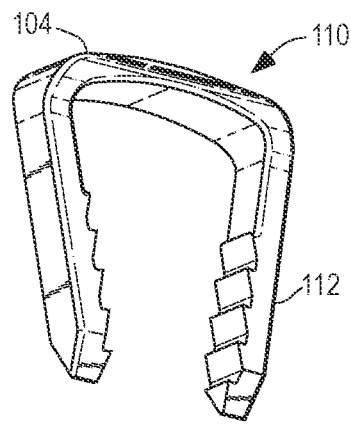
FIG. 20 is a perspective view of a surgical staple having two legs.
Figure 21:
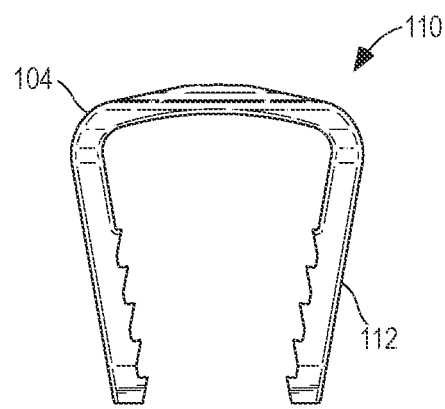
FIG. 21 is a side elevation view of the surgical staple of FIG. 20, showing legs of the staple at acute angles relative to a bridge.
Figure 22:
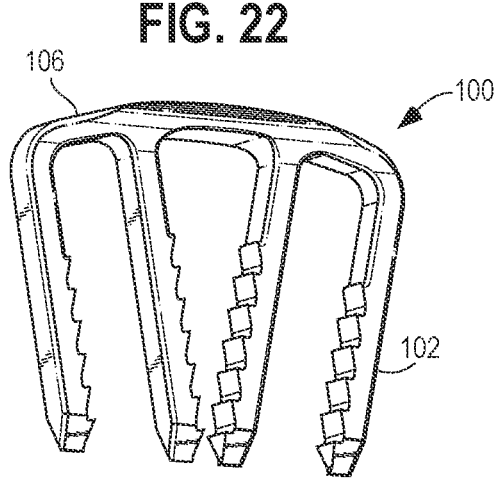
FIG. 22 is a perspective view of a surgical staple having four legs.
Figure 23:
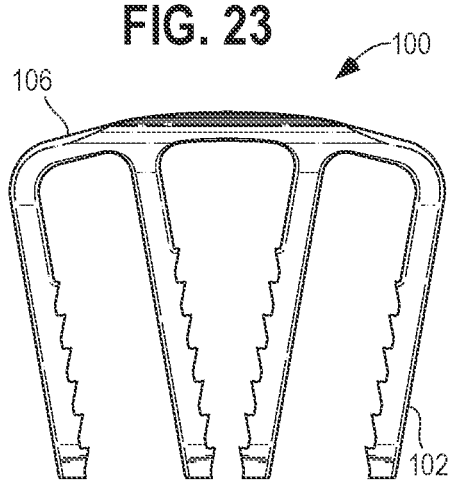
FIG. 23 is a side elevation view of the surgical staple of FIG. 22, showing legs of the staple at acute angle relative to a bridge.

A first embodiment of the guide tool 10 includes a rearward set of drill guides 12 fixed relative to a handle 14 and an adjustable forward set of drill guides 16 that can be selectively fixed relative to the rearward set of drill guides 12, aspects of which are shown in FIGS. 1-12. The guide tool 10 can be used for drilling guide holes in bones for insertion of a legs 102 of a first surgical staple 100 and legs 112 of a second surgical staple 110. The rearward drill guides 12 can be used to drill a plurality of parallel guide holes for receiving the legs 102 of the first staple 100 which, in the exemplary embedment, has four legs 102 generally in a first staple plane, such as those shown in FIGS. 22-25. The forward drill guides 16 can be used to drill a plurality of parallel holes for receiving the legs of the second staple which, in the exemplary embodiment, has two legs generally in a second staple plane, such as shown in FIGS. 20 and 21. The guide tool 10 is configured such that the holes are aligned so that the first and second staple planes intersect once the staples are inserted into the bones, as shown in FIG. 12.

Broadly, the guide tool 10 includes the handle 14 with an attached rearward set of drill guides 12. An adjustable arm 18 has a linear segment 20 that can be selectively attached to the handle 14 in a variety of different positions. The adjustable arm 18 also has an arcuate segment 22 that is spaced from the handle by the linear segment of the arm. A bracket 24 is slidable along the arcuate segment 22 and carries the forward set of drill guides 16. The bracket, and thus the forward set of drill guides, can be selectively fixed relative to the arcuate segment of the arm.

Each of the drill guides 12, 16 includes a cylindrical sleeve 26 having a through-opening extending along a central axis thereof. In use, a drill bit can be inserted into the through-opening and used to drill a hole. The through-opening and drill bit are preferably sized that play between the drill bit and the sleeve is minimized so that a hole can be drilled with accuracy. The drill guides also include a separate holder 28 for each of the cylindrical sleeves. Each of the holders includes a through-bore for receiving part of one of the cylindrical sleeves. Each of the cylindrical sleeves can optionally have a serrated edge at the distal tip thereof for seating on an adjacent bone.

The cylindrical sleeves are axially and rotationally secured in the through-bores of the holders. Each of the holders has a pair of aligned apertures tending perpendicular relative to a longitudinal axis passing through a center of the holder. An inner circumferential wall of the holder has partially dished in alignment with the aligned apertures. Each of the cylindrical sleeves also has a dished portion on an outer circumference thereof, extending generally perpendicular relative to the central axis thereof. When one of the cylindrical sleeves is received with the through-bore of one of the holders, the dished portion of the cylindrical sleeve is positioned to face the dished portion of the inner circumferential wall of the holder such that an opening of circular cross-section is formed therebetween. When so arranged, a pin can be positioned with each end being held by the aligned apertures and through the opening formed by the dished portions. The pin is thus fixed to the holder via the aligned apertures thereof. Engagement between the fixed pin and the dished portion of the cylindrical sleeve both prevents rotation of the cylindrical sleeve within the holder and axial movement of the cylindrical sleeve within the holder.

Figure 1:
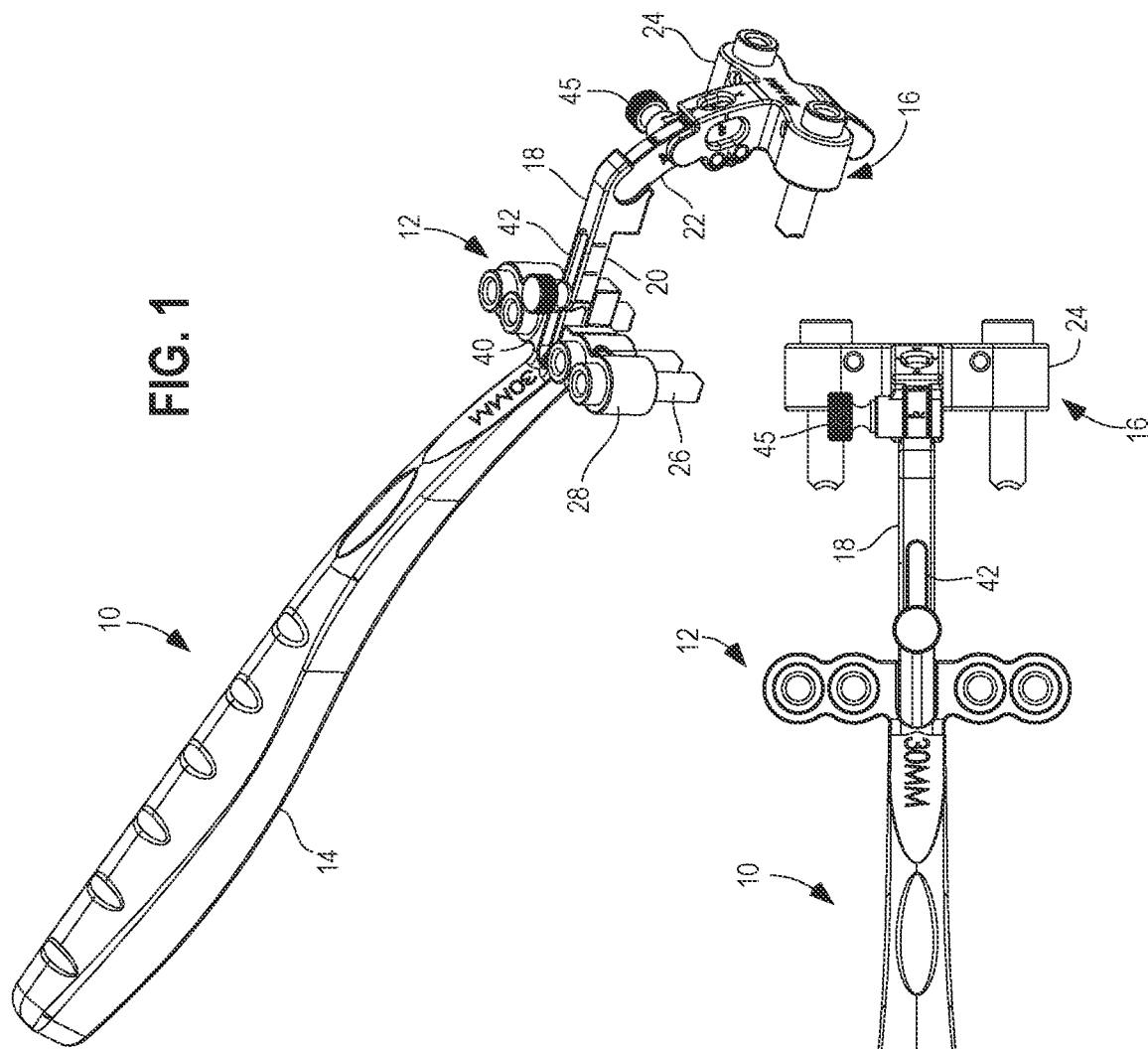
FIG. 1 is a perspective view of an embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple.
Figure 2:
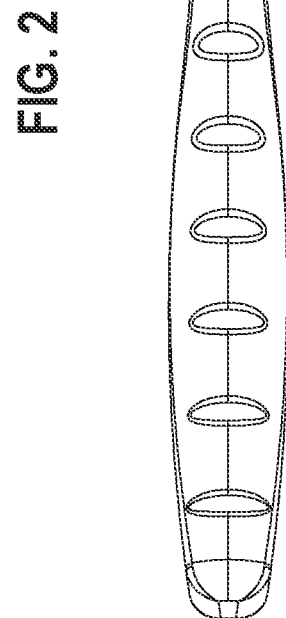
FIG. 2 is a top plan view of the guide tool of FIG. 1.
Figure 3:
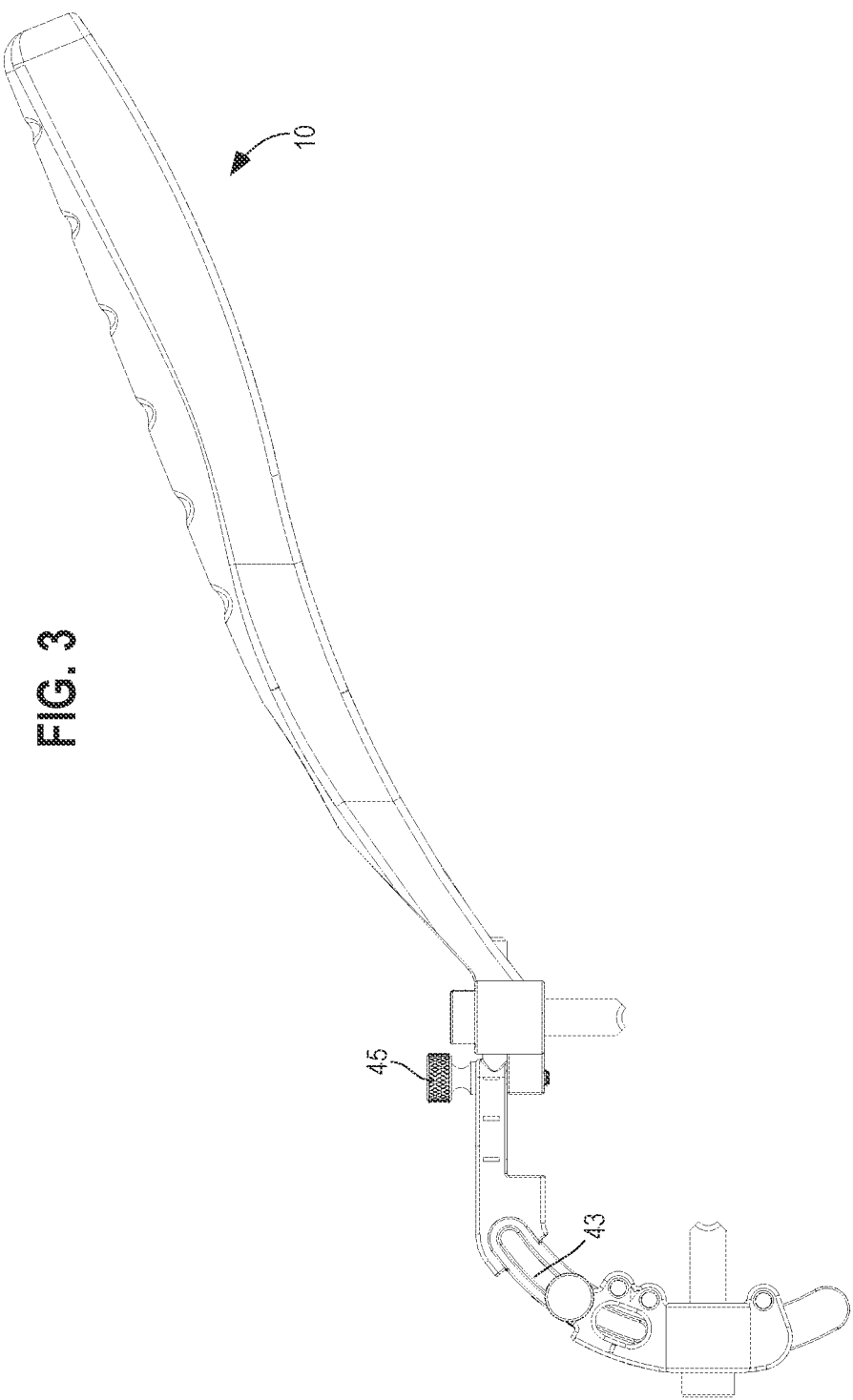
FIG. 3 is a left side elevation view of the guide tool of FIG. 1.
Figure 4:
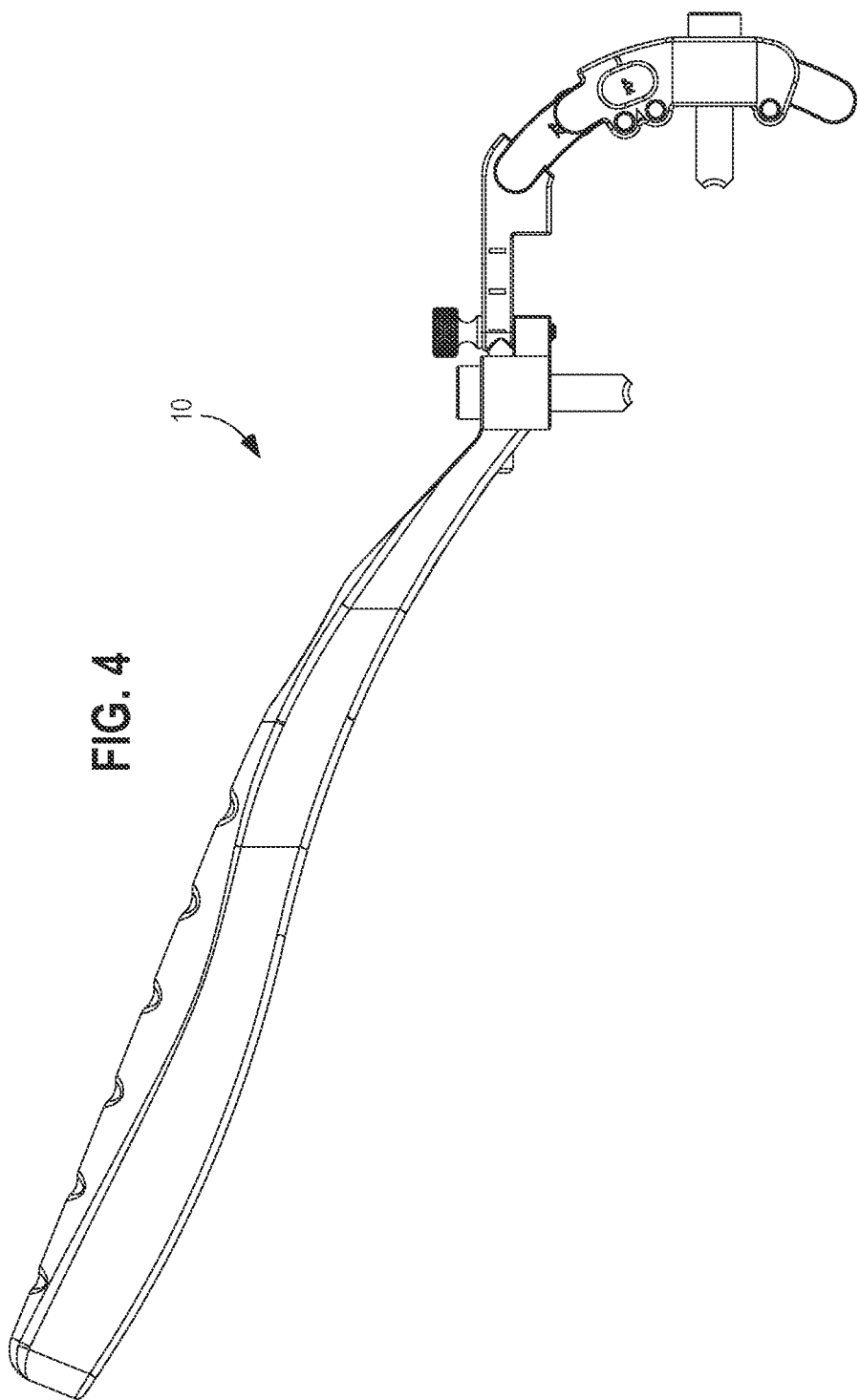
FIG. 4 is a right side elevation view of the guide tool of FIG. 1.
Figure 5:
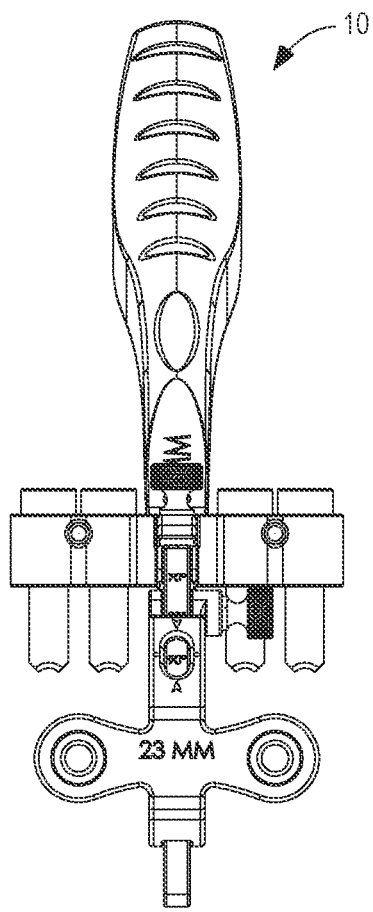
FIG. 5 is a front side elevation view of the guide tool of FIG. 1.

The handle 14 includes a longitudinally extending grasping portion, which can optionally be ergonomically contoured for being held by the hand of a surgeon or other user. As mentioned above, the rearward set of drill guides 12 are attached to the handle 14. More specifically, there are four drill guide holders integrally formed at end of the handle. The four holders are arranged in a line that is generally perpendicular to the grasping portion of the handle, as shown in FIG. 2. Other arrangements of the holders relative to the handle can be made, e.g., parallel or angled; and the holders do not have to be in a line, but can be in other non-linear arrangements. In the illustrated embodiment, there are four holders. It will be understood that a different number of holders can be used depending upon the number of staple legs to be inserted into holes, e.g., two, three, etc.

Figure 7:
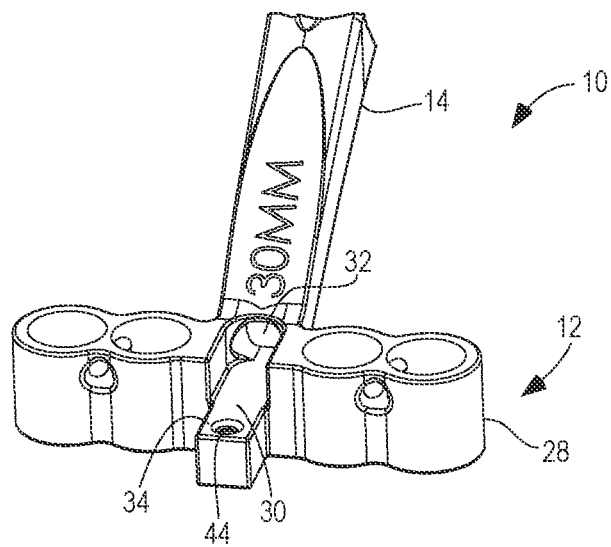
FIG. 7 is a detailed view of the front end of the handle of FIG. 1.
Figure 8:
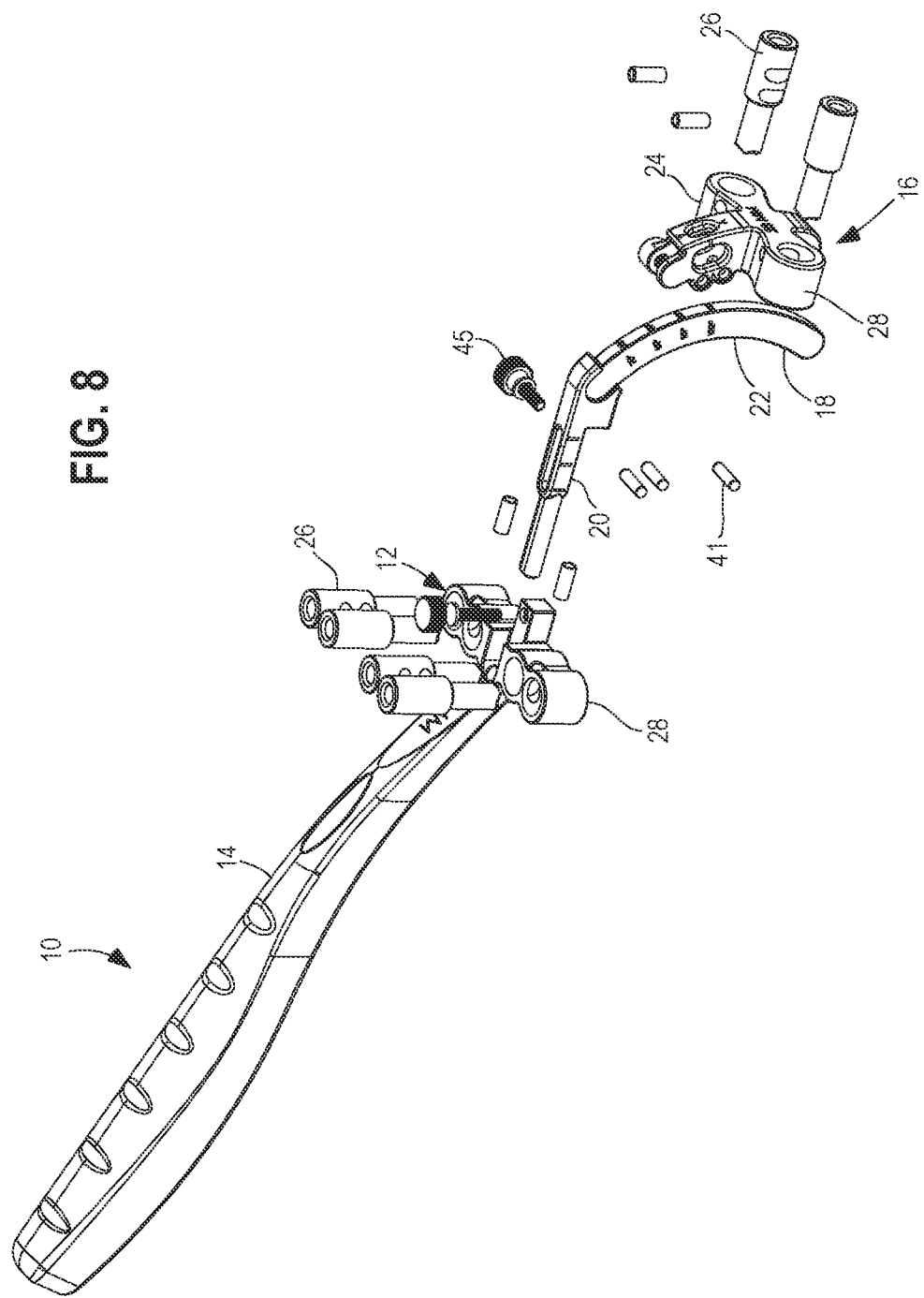
FIG. 8 is an exploded view of the guide tool of FIG. 1.
Figure 9:
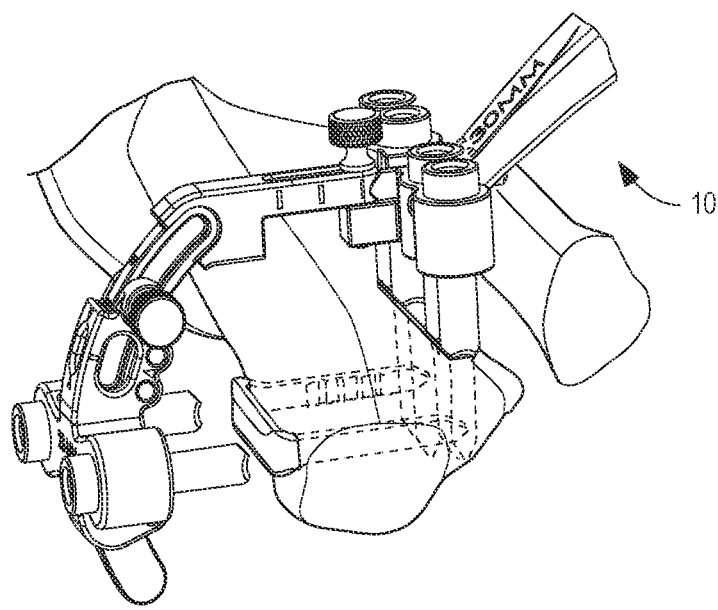
FIG. 9 is a perspective view of an operative portion of the guide tool of FIG. 1 positioned adjacent a bone in after guide holes have been drilled in the bone and staples inserted into the guide holes.

The handle includes an open channel 30 formed between the four holders, as seen in FIG. 7. The channel is configured to receive the linear segment of the adjustable arm. More specifically, two of the holders are on one side of the channel and two of the holders on another side of the channel. The channel has a flat bottom wall, a rear end with an obround opening 32, and a projecting end 34 extending forward of the holders. The linear segment of the adjustable arm terminates in a protuberance that is obround in cross-section and keyed to fit within the oval-shaped opening of the rear end of the channel of the handle. A flattened bottom of the protuberance abuts the flat bottom wall of the channel. Accordingly, engagement between the channel and the protuberance of the linear segment of the arm restricts rotation of the arm relative to the handle.

The arm can be selectively attached relative to the handle, as mentioned above. To that end, a threaded screw or knob 40 can be used to secure the arm to the handle. More specifically, the linear segment of the adjustable arm has an elongated slot 42 formed therein. When the protuberance of the linear segment of the arm is received within the channel of the handle, the slot is positioned above a threaded bore 44 formed in the projecting end of the channel. The knob has a threaded shaft depending from a head with a knurled periphery. The threaded shaft of the knob is inserted through the slot of the linear segment of the arm and into the threaded bore. Tightening of the knob can clamp the arm to the handle. The knob can be removed to either detach the arm from the handle or to loosened to allow the arm to be slidingly adjusted relative to the handle and then tightened.

Figure 6:
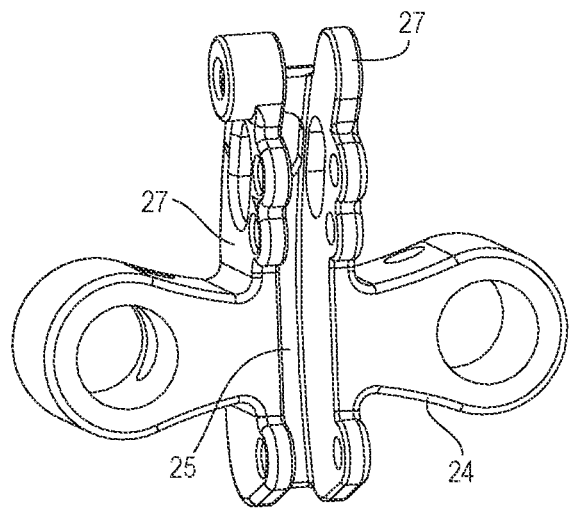
FIG. 6 is a rear perspective view of a movable bracket of the forward guides of the guide tool of FIG. 1.

The bracket 24, which carries the forward set of drill guides, is slidable along the arcuate segment. A pair of the holders are provided on the bracket, one on each side of the arcuate bottom wall thereof. The arcuate segment has an arcuate, radially outward surface and an arcuate, radially inward surface. The arcuate segment has a generally rectangular cross-section. The bracket includes an arcuate bottom wall 25, as shown in FIG. 6, with a pair of lateral, upstanding side walls 27. A radius of curvature of the bottom wall of the bracket generally matches a radius of curvature of the arcuate segment of the arm such that the bottom wall of the bracket can slide along the outward surface of the arcuate segment of the arm. Each of the pair of sidewalls has three apertures. The apertures of one of the pair of sidewalls is aligned with the apertures of the other of the pair of sidewalls. Pins 41 are inserted through aligned apertures, such that there are three pins. The apertures, and thus the pins, are aligned such the dowels can slide along the inward surface of the arcuate segment of the arm. The pins and the arcuate bottom wall sandwich the radially inward surface and the radially outward surface of the arcuate segment, respectively, therebetween.

The pair of sidewalls and the bottom walls optionally have windows formed therein through which indicia on the arcuate segment of the arc can be visible to help with positioning the bracket along the arcuate segment of the arm.

The bracket, and thus the forward set of drill guides, can be selectively fixed relative to the arcuate segment of the arm, as mentioned above. The arcuate segment of the adjustable arm has a generally rectangular cross-section. One side of the arcuate segment has a curved, obround-shaped groove 43. One of the sidewalls of the bracket has an extending ear with a threaded through-bore. A knob 45 is provided to secure the bracket on the arcuate segment of the arm. More specifically, the knob has a threaded shaft depending from a head with a knurled periphery. The threaded shaft of the knob is threaded into the threaded through-bore of the ear of the sidewall of the arcuate segment of the arm and into engagement with a bottom of the groove on the arcuate segment of the arm. Tightening of the knob can clamp the bracket to the arm. The knob can be removed to allow the bracket to be slid off the arm or loosened to allow the bracket to be slidingly adjusted relative to the arm and then tightened to fix the bracket in position relative to the rearward set of drill guides. Ends of the groove on the arcuate segment of the arm can limit the extent to which the backet can slide on the arm when then threaded shaft is received within the groove but not engaged with the bottom wall thereof.

Turning now to a method of using the first embodiment of the guide tool, the handle can be used to position the rearward set of drill guides against a pair of adjacent bones, as shown in FIG. 10. The forward set of drill guides can also be positioned against the pair of adjacent bones, also as shown in FIG. 10, with adjustment to the position of the forward set of drill guides being made using the arm and/or the bracket. As used herein, adjacent bones can also include bone pieces of the same bone that require fusion. Optionally, a guide wire for a cannulated screw can be installed in one of the bones. When used, the guide wire can then be threaded through one of the rearward set of drill guides to help with positioning the guide tool adjacent the bones. A first of the holes can then be drilled using a drill bit—attached to a drill—inserted through the first of the holes. A surgeon can drill the remainder of the holes or, optionally, insert one or more removable pins temporarily through the drill guides to temporarily secure the guide tool to the bone or bones. For example, a hole can be drilled into one of the pair of bones using one of the rearward set of drill guides to guide the drill bit; and another hole can be drilled into the same or a different one of the pair of bones using the forward set of drill guides to guide the drill bit, as shown in FIG. 11. Removable pins can be inserted into those holes to temporarily secure the guide tool to the bone or bones. The remainder of the holes can be drilled, after which the pins can be removed and the guide tool removed from adjacent the bones. Staples can then be inserted into the holes that are drilled into the bones to fuse the bones together, as shown in FIG. 12.

Preferably, though not necessarily, the legs of each of the staples in their resting or unbiased state are at acute angles relative to a bridge that joins the legs, as shown in FIGS. 20-25. The staples can optionally be made of a shape memory metal, such as nitinol. The drilled holes made using the rearward set of drill guides are perpendicular to each other, as are the drilled holes made using the forward set of drill guides. The legs of the staples can be temporarily bent to be generally perpendicular relative to the bridges and generally parallel relative to each other and, when in that arrangement, inserted into the holes. An insertion tool, such as that disclosed in U.S. patent application Ser. No. 17/322,580, filed May 17, 2021, which is hereby incorporated herein by reference in its entirety, can engage with the staple to bend and temporarily hold the legs in the perpendicular and parallel arrangement for insertion into the holes. Once the legs are almost completely inserted, the insertion tool can be disengaged from the staple and the staple legs inserted the rest of the way into the holes. Advantageously, the shape memory properties of the staple can cause the legs to want to return to their acutely angled orientation relative to the bridge, thereby compressing the adjacent bones together, preferably with a compressing force that is greater than if the legs in their resting or neutral state were generally perpendicular relative to the bridge.

Figure 13:
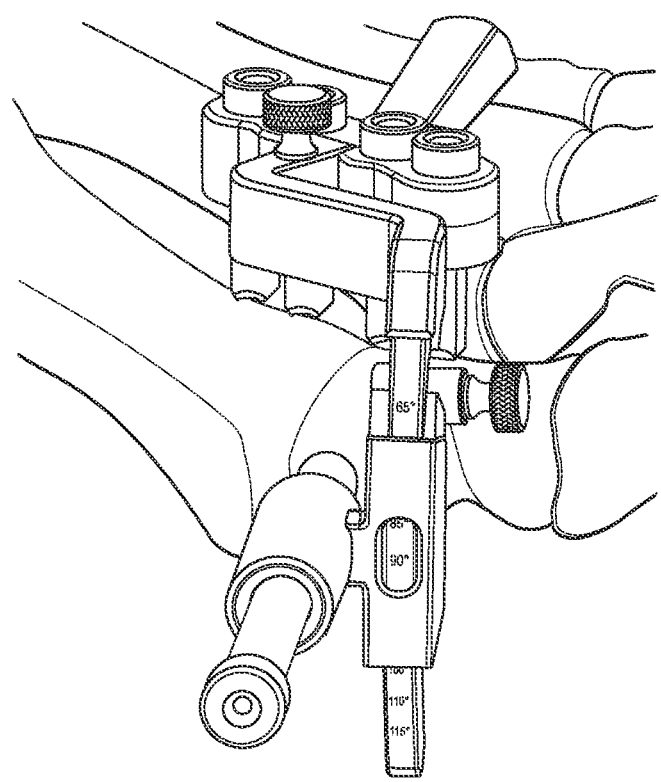
FIG. 13 is a perspective view of a second embodiment of a guide tool for use in drilling holes in bones for insertion of a surgical staple and a bone screw, the guide tool having a set of rearward guides for use in drilling holes to receive legs of the surgical staple and a moveable forward guide for use in drilling a hole to receive the bone screw, the guide tool being positioned adjacent bones for drilling holes.
Figure 14:
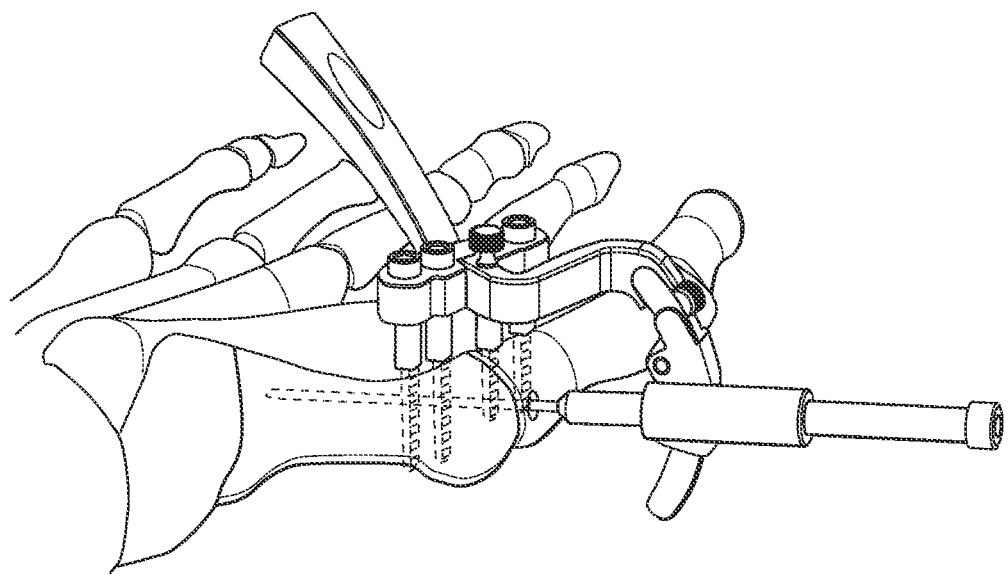
FIG. 14 is a different perspective view of the tool of FIG. 13 positioned adjacent bones for drilling holes, showing a guide wire inserted through a pin disposed in the forward guide.
Figure 15:
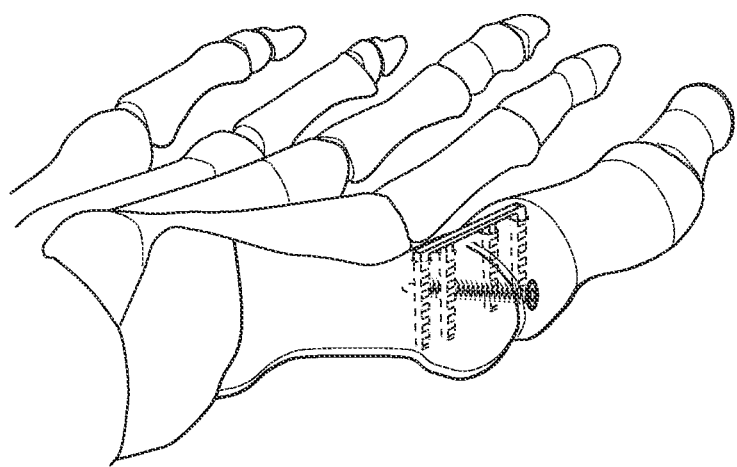
FIG. 15 is a perspective view of a staple and a screw having been inserted into holes drilled in the bones.

A second embodiment of the guide tool is shown in use in FIGS. 13 and 14, with like parts having like numbers as compared with the first embodiment of the guide tool. The second embodiment of the guide tool differs from that of the first embodiment in that instead of being used to drill holes for a first staple and a second staple, the guide tool is configured to drill holes for only the legs of one staple and another hole for a bone screw. In particular, the forward set of drill guides is replaced by a single drill guide. Because a bone screw is used instead of one of the staples, the bone screw must be inserted such that it spans between both bones; thus, the hole drilled for the bone screw must also span between both bones. This is accomplished by the length of the bone screw as well as the angle in which the bone screw is inserted. The forward drill guide is angled such that the drill bit drills a hole that is angled, i.e., not perpendicular, to a plane of the holes for the legs of the staple. The linear and arcuate segments of the adjustable arm are at an obtuse angle relative to each other, as shown in FIGS. 13 and 14, such that a hole drilled using the forward drill guide will is angled to a plate of the holes for the legs of the staple. Like the first embodiment, a guide wire can optionally be used for aligned the guide tool of the second embodiment with the bone or bones. The holes can be sequentially drilled using the drill guides and, optionally, one or more pins can be used for temporarily securing the guide tool to the bone or bones. After drilling of the guide holes, the staple and the screw can be inserted, as shown in FIG. 15.

Figure 16:
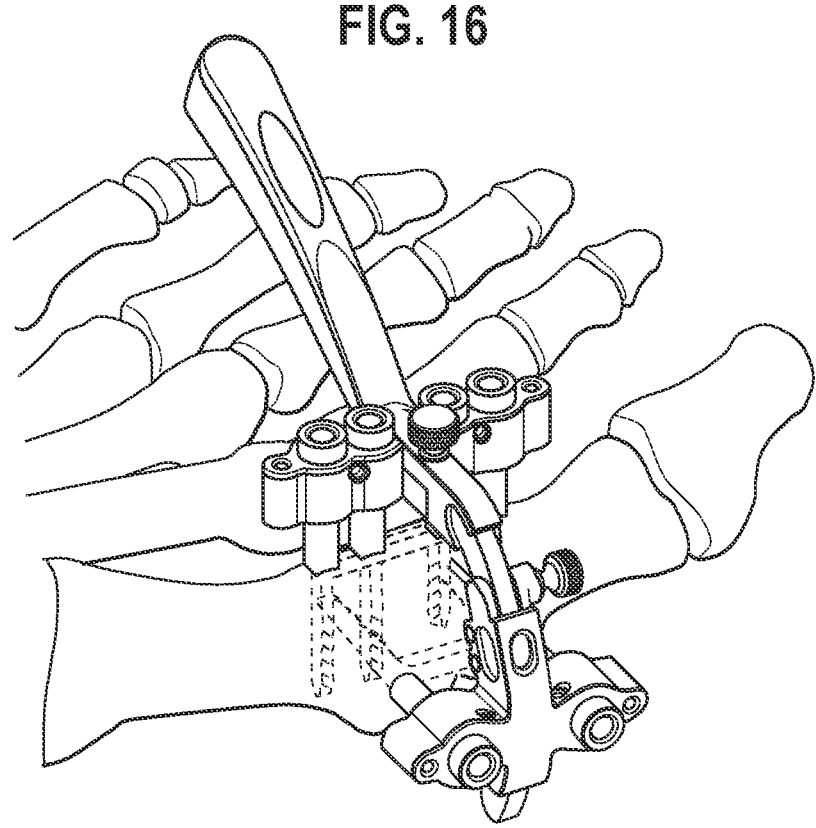
FIG. 16 is a perspective view of an alternative embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple, and having multiple openings through which guide pins can be inserted and passed into adjacent bones for positing the tool prior to the drilling of some or all of the guide holes.
Figure 17:
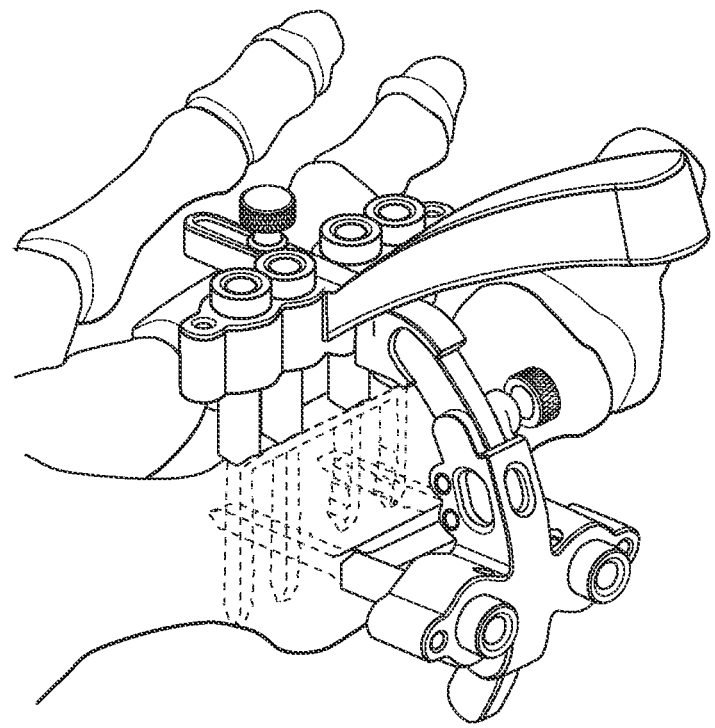
FIG. 17 is a perspective view of the tool of FIG. 16, showing guide holes having been drilled for the legs of the staples.

FIGS. 16 and 17 depict an alternative embodiment of a guide tool for use in drilling holes in bones for insertion of a first surgical staple and a second surgical staple, the guide tool having a set of rearward guides for use in drilling holes to receive legs of the first surgical staple and a moveable set of forward guides for use in drilling holes to receive legs of the second surgical staple. This embodiment differs from the first embodiment in that the handle is of a different size, the arm lacks the extension so that it can be inserted through a rear hole in the channel so that the handle is reversible, and there are multiple openings adjacent the drill guides through which guide pins can be inserted and passed into adjacent bones for positing the tool prior to the drilling of some or all of the guide holes. Any of these features can be incorporated into the other embodiments described herein. FIG. 17 shows guide holes having been drilled for the legs of the staples.

Figure 18:
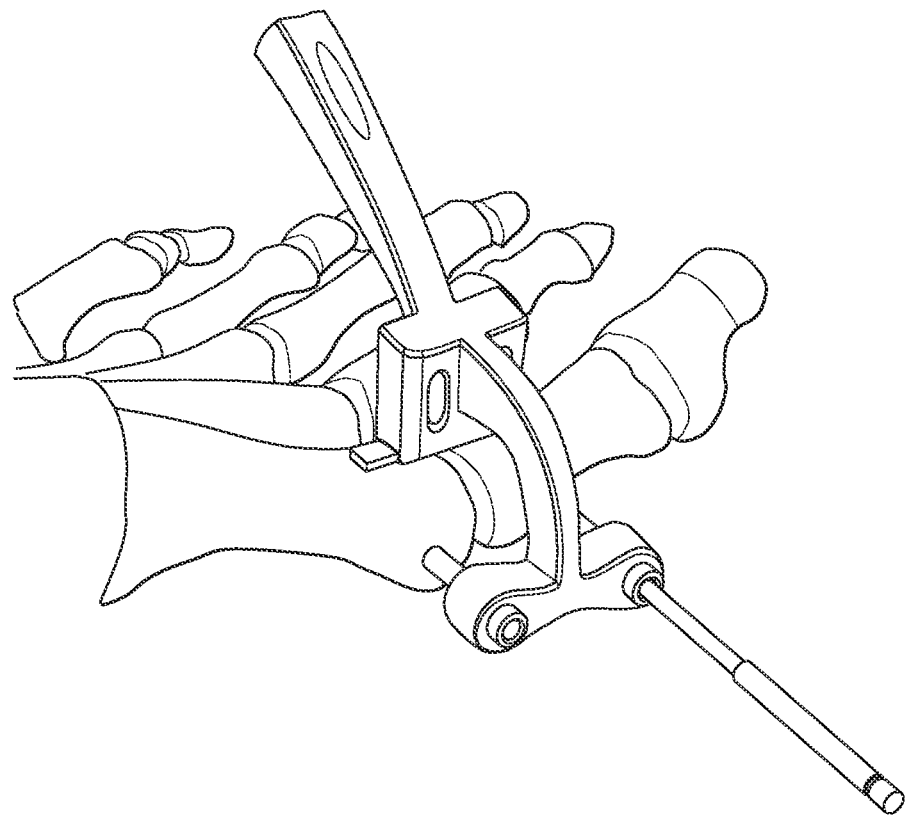
FIG. 18 is another alternative tool, having a portion that can clamp or at least partially anchor onto an already-inserted staple, and a forward portion with a pair of drilling guides.
Figure 19:
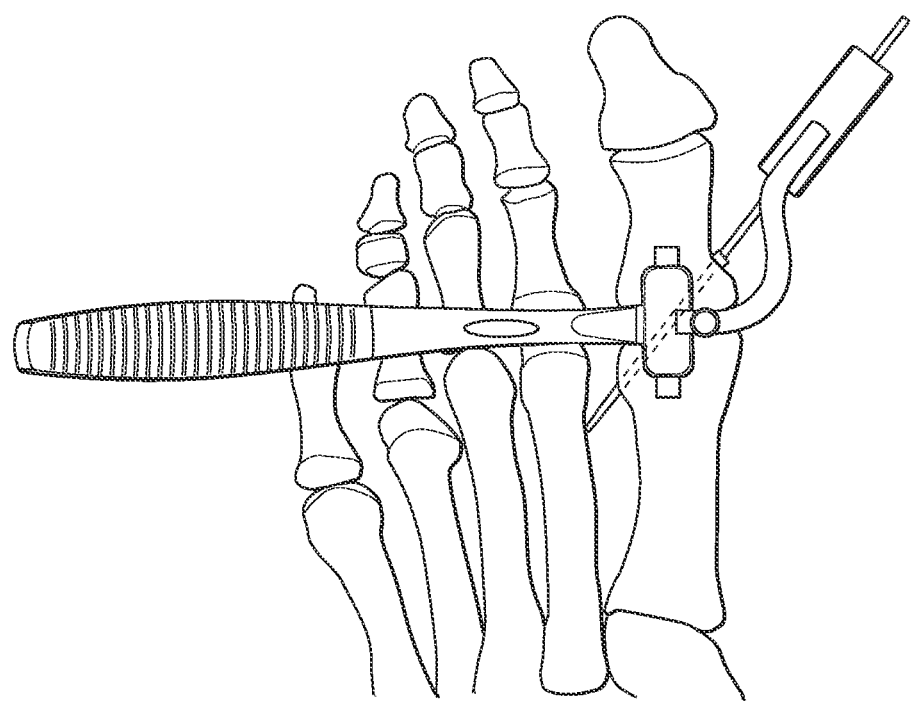
FIG. 19 is another alternative tool, having a portion that can clamp or at least partially anchor onto an already-inserted staple, and a forward portion with an offset drilling guide for drilling a guide hole for a screw.

FIGS. 18 and 19 depict addition alternative tools. Each of these two tools has a portion that can clamp or at least partially anchor onto an already-inserted staple, such as groove or slot for receiving the bridge of the staple. Each of these two tools also includes a forward portion with a pair of drilling guides (FIG. 18) for drilling guide holes for a staple, in the illustrated embodiment, a two-legged staple, or an offset drilling guide (FIG. 19) for drilling a guide hole for a screw.

Figure 24:
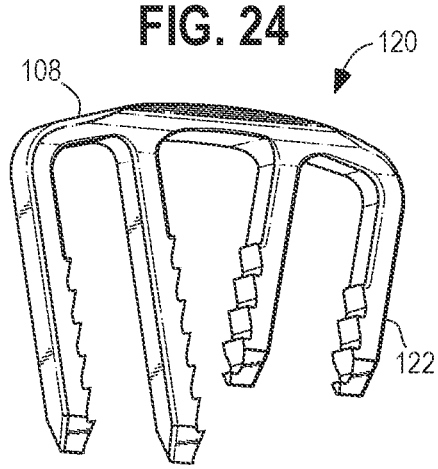
FIG. 24 is a perspective view of a surgical staple having four legs.
Figure 25:
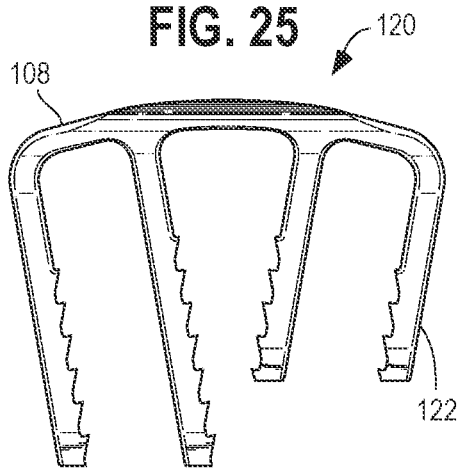
FIG. 25 is a side elevation view of the surgical staple of FIG. 22, showing legs of the staple at acute angle relative to a bridge.

FIGS. 20-25 disclose various embodiments of staples 100, 110, 120, some staples 110 with two legs 112 (FIGS. 20 and 21), some staples 100, 120 with four legs 102, 122 (FIGS. 22 and 23), and one 120 with four legs 122, two of which are shorter than the other two legs (FIGS. 24 and 25). The legs of the staples are connected via a bridge 104, 106, 108, and the legs can optionally have teeth such as those shown. The use of a staple with two legs shorter than another two legs can beneficially be used for various procedures, such as when one of the bones or the operative portion of the bone has a thickness that may not warrant or be suitable for a longer leg. Other shapes and sizes of staples can be used, such as those disclosed in U.S. patent application Ser. Nos. 29/804,413 and 29/804,411, each filed May 17, 2021, which are each hereby incorporated herein by reference in their entireties.

The staples are preferably, though not necessarily, made of nitinol or another shape memory material. Sleeves and arm can be made of surgical grade stainless steel, among other materials. The handle and bracket can also be made of surgical grade stainless steel, suitable thermoplastics, e.g., polyphenylsulfone (PPSU), or outer suitable materials.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A guide tool configured for drilling holes in bones for insertion of a legs of a first surgical staple and legs of a second surgical staple, the tool comprising:
    a handle;
    a rearward set of drill guides fixed relative to the handle;
    an adjustable arm selectively fixable relative to the handle and moveable toward and away from the rearward set of drill guides, the arm having an arcuate segment;
    a forward set of drill guides selectively fixable relative to the arcuate segment of the arm, the forward set of drill guides being movable along an arcuate path.

2. The guide tool of claim 1, wherein:
    each of the forward set of drill guides has a longitudinally extending opening with a central axis configured through which a drill bit can be inserted for drilling a hole in an adjacent bone; and
    each of the rearward set of drill guides has a longitudinally extending opening with a central axis, through which, in use, a drill bit can be inserted for drilling a hole in an adjacent bone.

3. The guide tool of claim 2, wherein one of the forward set and rearward set of drill guides includes four drill guides, comprising a first pair of adjacent drill guides and a second pair of adjacent drill guides, and another of the forward set and rearward set of drill guides includes two drill guides, comprising a first drill guide and a second drill guide, and wherein the arm is configured such that the central axis of the first drill guide projects between a projection of the central axes of the first pair of drill guides and the central axis of the second drill guide projects between a projection of the central axes of the second pair of drill guides.

4. The guide tool of claim 2, wherein the rearward set of drill guides includes four drill guides, comprising a first pair of adjacent drill guides and a second pair of adjacent drill guides, and the forward set of drill guides includes two drill guides, comprising a first drill guide and a second drill guide, and wherein the arm is configured such that the central axis of the first drill guide projects between a projection of the central axes of the first pair of drill guides and the central axis of the second drill guide projects between a projection of the central axes of the second pair of drill guides.

5. The guide tool of claim 1, wherein the forward set of drill guides are carried by a bracket that is slidable along the arcuate segment of the adjustable arm.

6. The guide tool of claim 5, further comprising means for selectively fixing the bracket relative to the arcuate segment of the adjustable arm.

7. The guide tool of claim 5, wherein each of the drill guides includes a sleeve with a through-bore for receiving, in use, a drill bit, the sleeves of the rearward set of drill guides being axially and rotationally fixed relative to the handle and the sleeves of the forward set of drill guides being axially and rotationally fixed relative to the bracket.

8. A method of drilling holes in bones for insertion of a legs of a first surgical staple and legs of a second surgical staple using the guide tool of claim 1, the method comprising:
    positioning the rearward set of drill guides adjacent the bones;
    positioning the forward set of drill guides adjacent the bones;
    fixing the position of the forward set of drill guides relative to the rearward set of drill guides;
    inserting a drill bit progressively through each of the drill guides of the rearward set of drill guides and drilling holes in the bones for receiving the legs of the first surgical staple; and
    inserting a drill bit progressively through each of the drill guides of the forward set of drill guides and drilling holes in the bones for receiving the legs of the second surgical staple.

9. The method of claim 8, further comprising:
    temporarily securing at least one of the rearward set of drill guides relative to at least one of the bones prior to drilling holes all of the holes for the legs of the first surgical staple; and/or
    temporarily securing at least one of the forward set of drill guides relative to at least one of the bones prior to drilling holes all of the holes for the legs of the second surgical staple.

10. The method of claim 8, wherein at least one of the holes in the bones for receiving the legs of the first surgical staple passes between an adjacent pair of the holes in the bones for receiving the legs of the second surgical staple; or wherein at least one of the holes in the bones for receiving the legs of the second surgical staple passes between an adjacent pair of the holes in the bones for receiving the legs of the first surgical staple.

11. The method of claim 10, further comprising inserting the legs of the first surgical staple into the holes drilled in the bones for receiving the legs of the first surgical staple and inserting the legs of the second surgical staple into the holes drilled in the bones for receiving the legs of the second surgical staple.

12. A guide tool configured for drilling holes in bones for insertion of a legs of a first surgical staple and legs of a second surgical staple, the tool comprising:
a handle;
a rearward set of drill guides fixed relative to the handle;
an adjustable arm selectively fixable relative to the handle and moveable toward and away from the rearward set of drill guides, the arm having an arcuate segment; and
a forward set of drill guides selectively fixable relative to the arcuate segment of the arm,
wherein the adjustable arm has a linear segment that slidingly engages with the handle.

13. The guide tool of claim 12, further comprising means for selectively fixing the linear segment of the adjustable arm relative to the handle.

14. A guide tool configured for drilling holes in bones for insertion of a legs of a surgical staple and a bone screw, the tool comprising:
a handle;
a rearward set of drill guides fixed relative to the handle for use in drilling holes for the legs of the surgical staple;
an adjustable arm selectively fixable relative to the handle and moveable toward and away from the rearward set of drill guides, the arm having an arcuate segment; and
a forward drill guide selectively fixable relative to the arcuate segment of the arm for use in drilling a hole for the bone screw, the forward drill guide being movable along an arcuate path.

15. The guide tool of claim 14, wherein:
each of the forward set of drill guides has a longitudinally extending opening with a central axis configured through which a drill bit can be inserted for drilling a hole in an adjacent bone; and
the rearward drill guide has a longitudinally extending opening with a central axis, through which, in use, a drill bit can be inserted for drilling a hole through a pair of adjacent bones.

16. The guide tool of claim 15, wherein the arm is configured such that the central axis of the rearward drill guide projects between a projection of the central axes of the forward set of drill guides.

17. The guide tool of claim 15, wherein each of the drill guides of the rearward set of drill guides includes a rotatable sleeve axially and rotationally fixed relative to the handle.

18. The guide tool of claim 14, wherein the forward drill guide is carried by a bracket that is slidable along the arcuate segment of the adjustable arm.

19. The guide tool of claim 18, further comprising means for selectively fixing the bracket relative to the arcuate segment of the adjustable arm.

20. A method of drilling holes in bones for insertion of a legs of a surgical staple and bone screw using the guide tool of claim 17, the method comprising:
positioning the rearward set of drill guides adjacent the bones;
positioning the forward drill guide adjacent the bones;
fixing the position of the forward drill guide relative to the rearward set of drill guides;
inserting a drill bit progressively through each of the drill guides of the rearward set of drill guides and drilling holes for the legs of the surgical staple in the bones; and
inserting a drill bit through the forward drill guide and drilling a hole for the bone screw through one of the bones and at least partially into another of the bones.

21. The method of claim 20, further comprising temporarily securing the rearward set of drill guides relative to at least one of the bones prior to drilling the holes for the legs of the surgical staple in the bones.

22. The method of claim 21, wherein the home for the bone screw passes between a pair of the holes for the legs of the surgical staple.

23. The method of claim 22, further comprising inserting the legs of the surgical staple into the holes for the legs of the surgical staple and inserting the bone screw into the hole drilled for the bone screw.

24. A guide tool configured for drilling holes in bones for insertion of a legs of a surgical staple and a bone screw, the tool comprising:
a handle;
a rearward set of drill guides fixed relative to the handle for use in drilling holes for the legs of the surgical staple;
an adjustable arm selectively fixable relative to the handle and moveable toward and away from the rearward set of drill guides, the arm having an arcuate segment; and
a forward drill guide selectively fixable relative to the arcuate segment of the arm for use in drilling a hole for the bone screw,
wherein the adjustable arm has a linear segment that slidingly engages with the handle.

25. The guide tool of claim 24, further comprising means for selectively fixing the linear segment of the adjustable arm relative to the handle.

* * * * *